US009808270B2

(12) United States Patent
Tah et al.

(10) Patent No.: US 9,808,270 B2
(45) Date of Patent: Nov. 7, 2017

(54) MEDICAL RETRIEVAL DEVICES AND METHODS

(71) Applicant: Boston Scientific Scimed, Inc., Maple Grove, MN (US)

(72) Inventors: Richard C. Tah, Framingham, MA (US); Ronald Ciulla, Westford, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 302 days.

(21) Appl. No.: 14/570,230

(22) Filed: Dec. 15, 2014

(65) Prior Publication Data

US 2015/0173783 A1   Jun. 25, 2015

Related U.S. Application Data

(60) Provisional application No. 61/920,614, filed on Dec. 24, 2013.

(51) Int. Cl.
*A61B 17/22* (2006.01)
*A61B 17/221* (2006.01)

(52) U.S. Cl.
CPC .... *A61B 17/221* (2013.01); *A61B 2017/2215* (2013.01)

(58) Field of Classification Search
CPC ....................... A61B 17/221; A61B 2017/2215
See application file for complete search history.

(56) References Cited

U.S. PATENT DOCUMENTS

| 4,611,594 A | 9/1986 | Grayhack et al. |
| 6,245,087 B1 | 6/2001 | Addis |
| 6,383,195 B1 | 5/2002 | Richard |
| 2005/0131449 A1* | 6/2005 | Salahieh ................. A61F 2/013 606/200 |
| 2007/0027456 A1* | 2/2007 | Gartner .............. A61B 17/0057 606/113 |
| 2009/0222035 A1* | 9/2009 | Schneiderman ..... A61B 17/221 606/200 |
| 2010/0042107 A1* | 2/2010 | Merrifield ............ A61B 17/221 606/106 |
| 2011/0098738 A1 | 4/2011 | Hunt et al. |
| 2013/0018387 A1 | 1/2013 | Diamant et al. |

FOREIGN PATENT DOCUMENTS

| WO | WO 2007/110864 A2 | 10/2007 |
| WO | WO 2010/019776 A2 | 2/2010 |

* cited by examiner

*Primary Examiner* — Richard Louis
(74) *Attorney, Agent, or Firm* — Bookoff McAndrews, PLLC

(57) ABSTRACT

A retrieval device includes a sheath having a distal end, and a plurality of support members extending distal of the distal end, the support members each including a distal loop. The retrieval device further includes a hollow member extending distal of the distal end, and a movable member extending distally from the hollow member and slidably extending through the distal loops of the support members.

19 Claims, 5 Drawing Sheets

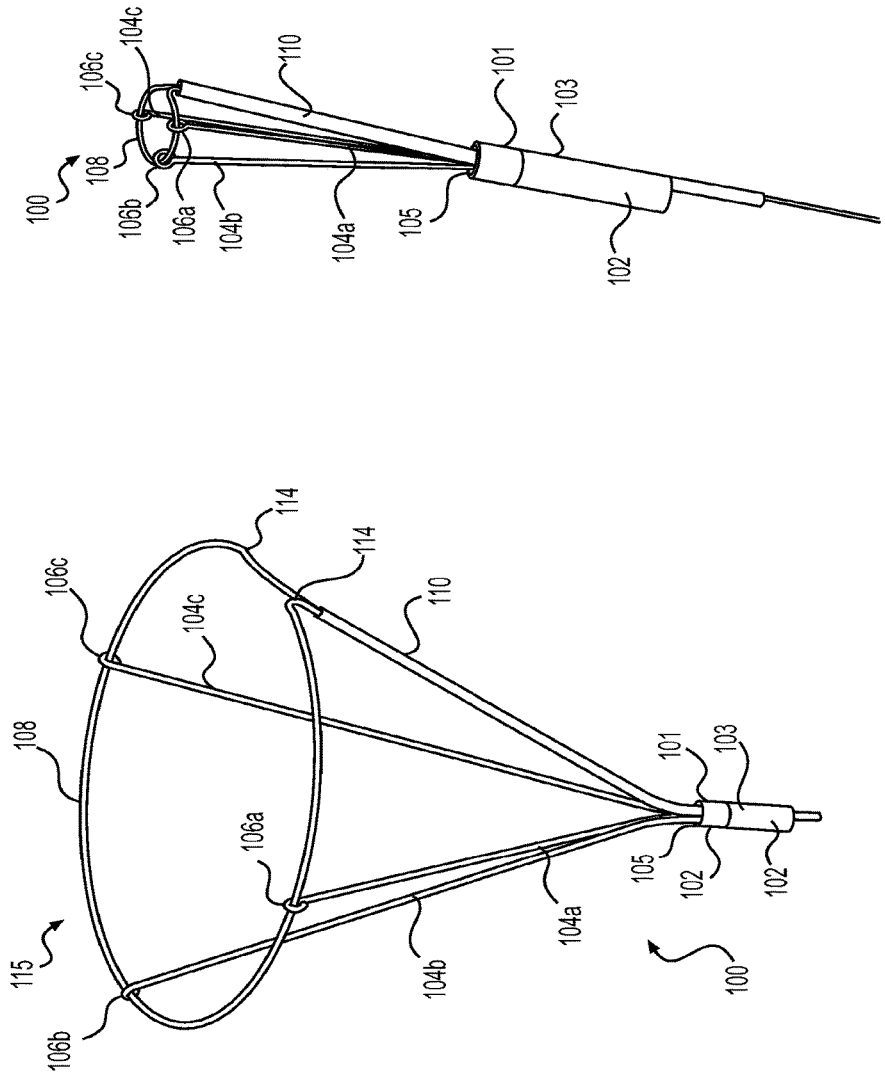

MEDICAL RETRIEVAL DEVICES AND METHODS

CROSS REFERENCE TO RELATED APPLICATIONS

This application claims the benefit of U.S. Provisional Application No. 61/920,614, filed Dec. 24, 2013, the disclosure of which is incorporated herein by reference in its entirety.

TECHNICAL FIELD

The present disclosure relates to medical devices and associated methods, and in particular, to medical retrieval devices for removing biological and/or foreign material from the body, and method of use and manufacture.

BACKGROUND

Medical retrieval baskets are used to retrieve biological and foreign material (such as stones) from the body. Some of these baskets may be used through an endoscope or a laparoscope. Stones or other biological materials are captured in the basket by moving the basket around the material to be retrieved, and maneuvering the material into the basket through spaces defined between basket legs.

However, it can be difficult to release captured material from such retrieval baskets, if such release is required or otherwise intended or relevant. Also, in some patients with long-standing clinical problems with urinary tract stones, a cicatrix may form in the tract as a result of trauma to its lining. The stenosis created by the cicatrix may not be so narrow as to interfere with insertion of a retrieval basket while the basket is in a closed position. However, after the basket is expanded to capture a stone that is lodged beyond the stenotic area of the tract, the diameter of the basket with the captured stone disposed therein may exceed the diameter of the stenotic region of the urinary tract. Under these circumstances, the stone needs to be released from the basket in order to withdraw the device from the urinary tract. If the stone cannot be released, then more invasive, surgical approaches are required to disengage the stone from the basket.

Also, in order to capture stones, related art baskets must be eased beyond the stone or to one side of the stone. This maneuver can be technically very difficult. The narrow diameter of the tract lumen, compounded by the formation of stretch resistant scar tissue in the tract at the sites of the stone, can limit or even severely limit the space around which the basket can maneuver. Moreover, the tract lining may become so attenuated at the site of the stone that advancing the basket to one side of the stone may risk rupture of the tract.

The present disclosure addresses one or more of the problems noted above and/or other problems in the art.

SUMMARY OF THE DISCLOSURE

Some embodiments are directed to several alternative designs and methods of using and manufacturing medical device structures, and in particular assemblies for removing a biological or foreign material (such as a stone) from a patient's body.

Accordingly, one exemplary embodiment includes a retrieval device having a sheath, multiple support members, a hollow member, and a movable member. The support members extend distal of a distal end of the sheath, and each support member includes a distal loop. The movable member extends distally through the hollow member, while slidably extending through the distal loops of the support members.

In addition or alternatively, another exemplary embodiment includes a retrieval device having a sheath, multiple capture members, and a loop member. The capture members extend distal of a distal end of the sheath. Each capture member has a loop, such that the loop member extends through the loops of the capture members.

In addition or alternatively, yet another exemplary embodiment is directed to a retrieval device having a sheath, multiple support members, and a loop member. The support members extend distal of the distal end of the sheath. Each support member has a loop, such that the loop member extends through the distal loops of the support members.

Additional characteristics, features, and advantages of the described embodiments will be set forth in part in the description that follows, and in part will be apparent from the description, or may be learned by practicing the disclosure. The disclosed subject matter can be realized and attained by way of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The accompanying drawings, which are incorporated in, and constitute a part this specification, illustrate exemplary embodiments of the present disclosure, and together with the description, serve to explain the principles of the disclosure.

FIG. 1 is a schematic view of a portion of an exemplary retrieval device according to an embodiment of the present disclosure.

FIG. 2 is a schematic view of the retrieval device of FIG. 1 configured and arranged in a partially closed configuration.

DETAILED DESCRIPTION

Figure 4:
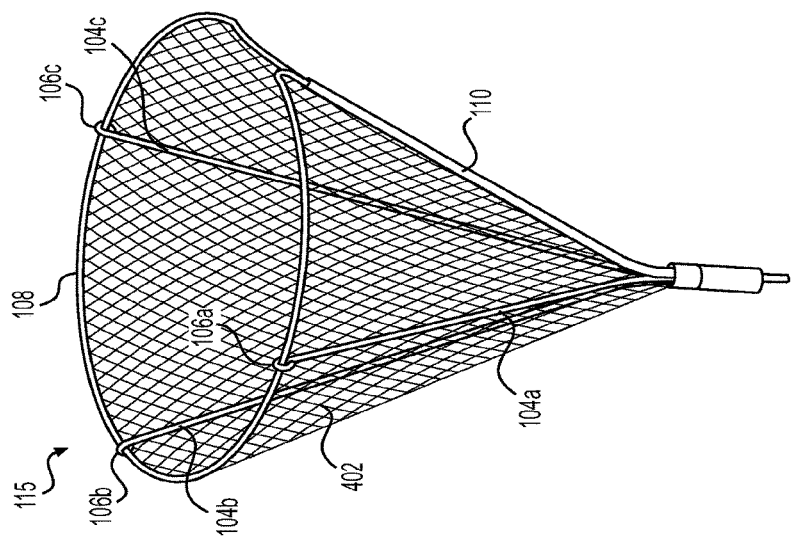
FIG. 4 is a schematic view of the retrieval device of FIG. 1 having a mesh.

Reference will now be made to embodiments of the present disclosure, examples of which are illustrated in the accompanying drawings. Wherever possible, the same reference numbers will be used throughout the drawings to refer to the same or like parts.

In the following disclosure, the term "distal" refers to the end farthest away from a medical professional when introducing a device in a patient. The term "proximal" refers to the end closest to the medical professional when placing a device in the patient. However, these terms are only used for explanatory purposes, and are not intended to limit the scope of the invention with regard to issues not directly related to the various disclosed concepts. As used in this disclosure, the terms "general" and "substantially" are used to express the possibility of minor variations in the value or feature. To the extent such terms require more definiteness, the minor variation is in the range of up to 10% deviation.

FIG. 1 is a schematic view of an exemplary retrieval device 100 configured to retrieve a biological and/or foreign material (for example, a stone) from a patient's body. The retrieval device 100 may include a sheath 102, multiple support members or capture members 104a, 104b, and 104c (collectively referred hereinafter as support members 104), a hollow member 110, and a movable member 108. The support members 104, hollow member 110, and movable member 108 together form a basket 115 having a generally conical open configuration that tapers in a proximal direction toward the sheath 102. Each component along with other components of the retrieval device 100 will now be discussed in detail.

The sheath 102 has a tubular shape defining a circular cross-section. Those skilled in the art will appreciate that the sheath 102 can alternatively define other suitable cross-sections, such as oval, etc. The sheath 102 may define a proximal end (not shown), a distal end 103, and a lumen 105 extending therebetween. The proximal end of the sheath 102 may be coupled to a handle in any conventional manner. The lumen 105 may extend through the entire length of the sheath 102, and may be configured to slidably receive one or more drive wires coupled to an actuation member associated with the handle of the device (not shown). In some embodiments, the sheath 102 may include any suitable number of lumens and/or corresponding openings for a variety of purposes, such as for receiving additional medical devices.

The sheath 102 may be formed of any suitable biocompatible and/or compliant materials, such as, for example, polymers, metals, alloys, either in combination or alone. The material or materials employed may be sufficiently stiff to enable use in various lumen diameters, and be sufficiently flexible to maneuver through tortuous and/or stenotic lumens, reducing, minimizing or even avoiding any undesirable tissue injuries. The materials employed to manufacture the sheath 102 may include a super elastic material or shape memory material, such as, for example, Nitinol. Other suitable materials may include polyether block amide, polyurethane, etc.

The support members 104 may be operably attached adjacent the distal end 103 of sheath 102, and extending distally and radially outwards therefrom. For example, each support member 104 may be fixedly attached to a ring member 101 extending from a distal end of the sheath 102. The support members 104 may be fixed in any conventional manner, such as by glue, weld, melting, molding, etc.

Support members 104 may be formed of any suitable material including, but not limited to, metals, polymers, or a combination of materials. In one embodiment, support members 104 may each include a metal wire. In an alternative embodiment, support members 104 may each be formed from two or more metals that are co-drawn together. Support members may comprise 2 or more filaments twisted together. Support members 104 may have any suitable cross-sectional profile such as, e.g., circular or oval. In some embodiments, portions of support members 104 may be flattened, machined, extruded, drawn, or etched into a different profile than a remaining portion of support members 104. In some embodiments, support members 104 may be pre-bent and/or slotted to allow deflection or directional bending. In one embodiment, support members 104 may be formed with a super elastic material or a shape memory material, such as, e.g., Nitinol wires having a diameter of about 0.003", although other suitable diameters may alternatively be utilized.

Each support member 104a, 104b, and 104c may have a distal loop or eyelet 106a, 106b, and 106c (collectively referred hereinafter as distal loops 106), respectively, located at a distal-most location on the respective support members 104. The distal loops 106a, 106b, and 106c may be configured to slidably engage with the movable member 108. Although the embodiment of FIG. 1 includes three support members 104a, 104b, and 104c, any suitable number of support members 104 may be employed, for example 4, 5, or 6, or more support members 104.

The hollow member 110 may include a tubular body extending distally and radially outwards, similar to the structure and/or configuration of the support members 104. The hollow member 110 may be fixedly coupled to the sheath 102 similar to the support members 104. As shown in FIG. 1, in one embodiment, hollow member 110 may extend more proximally within the lumen 105 of sheath 102 than support members 104. The hollow member 110 may slidably receive the movable member 108.

Movable member 108 may be received within hollow member 110 such that the two ends of movable member are located proximal the proximal end of the hollow member 110. Thus, the hollow member slidably receives two parallel portions of the movable member 108. Hollow member may have 2 lumens, one for each portion of the moveable member. Each end of the movable member 108 may be coupled to the handle in any conventional manner, such as via one or more pull wires coupled to an actuator for slidably moving movable member 108 proximally and distally within hollow member 110. It is understood that alternative configurations are possible, such as movable member 108 being formed of two separate but joined members, such as a ring member fixed to a longitudinally extending member.

When the movable member 108 is extended distally out the hollow member 110, the retrieval device 100 moves toward an open configuration as shown in FIG. 1. In the open configuration, the movable member 108 may form a ring-shaped configuration that lies in a plane at an angle to, for example generally normal to the longitudinal axis of the sheath 102. The distal loops 106 at the distal ends of the support members 104 slidably receive the movable member 108 so that the support members 104, hollow member 110, and movable member 108 together form a basket 115 having a generally conical open configuration that tapers in the proximal direction toward the sheath 105. It is understood that the movable member 108 may take the form of any continuous configuration other than the ring-shape depicted in FIG. 1. For example, an oval, square, diamond, or other shape may be formed.

Movable member 108 may be formed of any suitable material including, but not limited to, metals, polymers, or a combination of materials. The stiffness of movable member 108 may be selected so as to support movement into the open, circular configuration shown in FIG. 1. In one embodiment, movable member 108 may include a metal wire. In an alternative embodiment, movable member 108 may be formed from two or more metals that are co-drawn together. Movable member 108 may have any suitable cross-sectional profile such as, e.g., circular or oval. In some embodiments, portions of movable member 108 may be flattened, machined, extruded, drawn, or etched into a different profile than a remaining portion of movable member 108. In some embodiments, movable member 108 may be pre-bent and/or slotted to allow deflection or directional bending. For example, movable member 108 may be pre-bent to form the ring-shape configuration shown in FIG. 1 with proximally extending bends 114. In one embodiment, movable member 108 may be formed with a super elastic material or a shape memory material, such as, e.g., Nitinol wires having a diameter of about 0.003", although other suitable diameters may alternatively be utilized.

The retrieval device 100 may be configured to transition from the closed configuration shown in FIG. 2 to the open configuration shown in FIG. 1 by moving the movable member 108 distally by an actuator at the handle (not shown). Pulling the movable member 108 proximally by the actuator transitions the retrieval device 100 from an open configuration to a closed configuration. In the open configuration, the retrieval device forms an open ended, cone-shaped arrangement that allows for the grabbing and capturing of biological and/or foreign material (for example, stones), whereas in the closed configuration, the retrieval device 100 forms a collapsed profile for delivery or withdrawal of the retrieval device 100, or a trapping configuration to securely hold captured material in the basket 115. One or more, or all, of the elements making up the basket 115 of the retrieval device 100 (e.g., support members 104, hollow member 110, and movable member 108) may be pre-bent or biased toward the open configuration. The basket shape may flare outwards, inwards or not at all or comprise a combination of any configuration.

FIG. 2 is a schematic view of the retrieval device 100 in the closed configuration. Here, the movable member 108 has been pulled proximally, so that the support members 104, and in particular, the distal loops 106, slide along the movable member 108 and move radially in to decrease the radial size of the basket 115. This movement also reduces the overall diameter of the substantially ring-shaped portion of the movable member 108. In the closed configuration, the retrieval device 100 can be withdrawn into a catheter or similar device (not shown) to remove the retrieval device 100 from the patient's body. In a similar manner, the retrieval device 100 can be deployed to a desired location in the patient's body through the catheter or similar device.

Figure 3:
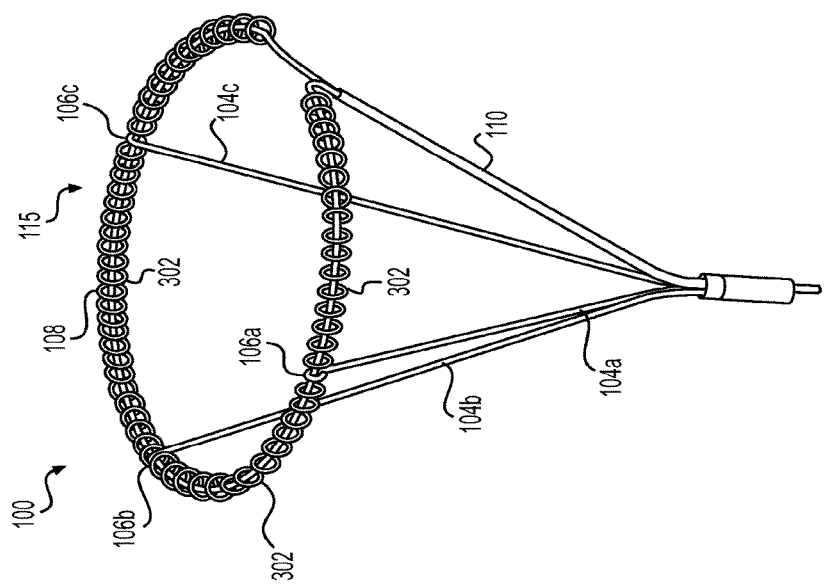
FIG. 3 is a schematic view of the retrieval device of FIG. 1 including a biasing member.

FIG. 3 shows another embodiment of the retrieval device 100. In addition to the features discussed above with respect to the retrieval device 100, the retrieval device 100 may include a biasing member, such as one or more coils 302. The coils 302 may extend between the support members 104 and around the movable member 108. For example, four coils 302 may extend between stops formed by either a distal loop 106 of a support member 104, or a distal end of hollow support member 110, and the coils 302 may be slidably received around the movable member 108. It is understood that the coils 102 could include a wider pitch than that shown in FIG. 3 to help in reducing the profile of the basket in the closed configuration. Further, less coils can be used, such as one, two, or three coils 302. Further, the distal ends of the support members 104 themselves may form one or more of the coils 302. One coil 302 could be used to extend along the movable member 108 between more than just two support members 104, e.g., around the entire ring formed by the movable member 108. Finally, it is understood that other types of biasing members (e.g. biasing ribbon) could be used instead of the coils 302.

The coil 302 may include any suitable resilient member, such as a spring, or the like. The coil 302 may be formed of any suitable biocompatible material such as, but not limited to, metals, polymers, alloys, or the like. The one or more coils 302 may facilitate proper and/or uniform spacing of the support members 104 along the basket 115 during movement between open and closed configurations. The one or more coils 302 may also provide a bias to urge the basket 115 toward the open configuration.

FIG. 4 shows another embodiment of the retrieval device 100. In addition to the features discussed above with respect to the retrieval device 100 (FIGS. 1-3), the retrieval device 100 may also include a mesh 402. The mesh 402 may encompass only a portion, or substantially all, of the basket 115 formed by the support members 104, hollow member 110, and the movable member 108. For example, the mesh 402 may be formed of any suitable strand or fiber material and be slidably coupled to each of the support members 104, hollow member 110, and the movable member 108 in a manner that allows the basket 115 to move between the open and closed configurations. The mesh 402 may facilitate enhanced retrieval by holding a captured stone within the basket. The mesh 402 may also impede or avoid any inadvertent bunching of the support members 104, thereby reducing or preventing formation of a space through which the captured stone may escape. Those skilled in the art will appreciate that the mesh 402 may be arranged in any cell configuration without departing from the scope and spirit of the present disclosure. The mesh 402 may comprise one filament or any number of intersecting or interlocking filaments. The position of mesh 402 on the support members 104 may be across all openings between the support members 104, or just a portion of an openings. Further, with the use of the mesh 402, a lesser number of support members 104 may be used.

Figure 5:
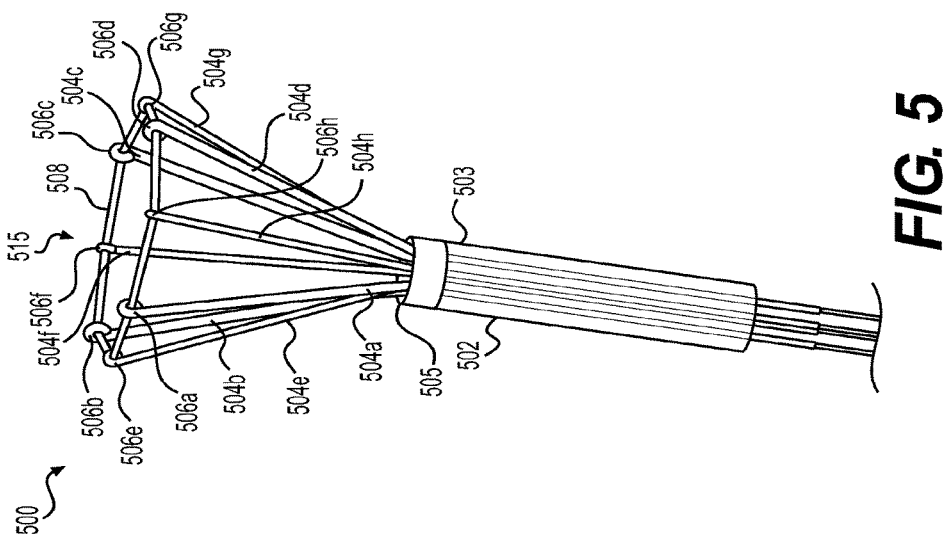
FIG. 5 is a schematic view of a retrieval device according to another embodiment of the present disclosure.

FIG. 5 illustrates a retrieval device 500 according to another embodiment of the present disclosure. The device 500 may include a sheath 502 having a distal end 503. Other major components of the retrieval device 500 may include multiple support members 504a, 504b, 504c, 504d, 504e, 504f, 504g, and 504h (collectively referred as support members 504) and a loop member 508. The support members 504 and loop member 508 together form an open-ended basket 515 having a generally conical open configuration that tapers in a proximal direction toward the sheath 502. The sheath 502, support members 504, and loop member 508 may be similar in structure, material, and/or function to the sheath 102, support members 104, and movable member 108, respectively, of the retrieval device of FIGS. 1-4.

Figure 6:
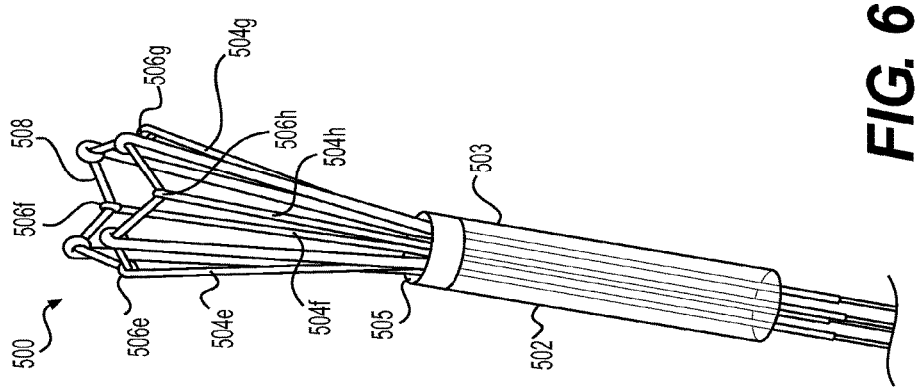
FIG. 6 is a schematic view of the retrieval device of FIG. 5 that is configured and arranged in a closed configuration.

The support members 504 may be further classed as a first array of support members 504a-504d, and a second array of support members 504e-504h, each extending distally and radially outwards from the distal end 503 of the sheath 502. The support members 504 may each include distal loops or eyelets 506, respectively, which may be located at a distal-most location on the support members 504 and are used to permanently attach the loop member 508 to the supporting members 504. In one embodiment, the first array of support members 504a-504d may be fixedly attached to the distal end 503 of the sheath 502, whereas the second array of support members 504e-504h may be longitudinally movable along and/or within the sheath 502 to move the retrieval device 500 between the open and closed configurations. The loop member 508 maybe preformed to easily bend at the regions of permanent attachment to the support members 504. For example, the loop member 508 could be configured with a flexibility to "hinge" at the attachment areas. The second array of support members 504e-504h may be attached proximally to a handle and actuator (not shown)

disposed outside of the patient's body to effectuate the bending or unbending of the loop member 508 at the hinge locations (at eyelets 506) to transition the basket 515 between the close and open configurations. While the first array of support members 504a-504d are shown in FIGS. 5 and 6 as having a different size than the second array of support members 504e-504h, it is understood that the first and second arrays may be the same size.

The support members 504a-504h may be arranged circumferentially, such that alternating support members 504a-504h may be longitudinally fixed and longitudinally movable. In other words, each fixed support member 504a-504d is disposed adjacent a longitudinally movable support member 504e-504h. Those skilled in the art, however, will appreciate that the two arrays of support members 504a-504h may be arranged in any particular manner to accomplish the above disclosed or other functions.

Loop member 508 may include a ring-shaped structure extending through the distal loops 506a-506h of the support members. The loop member 508 may lie in a plane generally normal to the longitudinal axis of the sheath 502. The distal loops 506 may be attached to the loop member 508 to form a cone-shaped configuration in an open configuration (as shown in FIG. 5). In particular, the support members 504a-504h along with the loop member 508 may form a conical shape when the device is in a fully open configuration.

The retrieval device 500 may be configured to transition between a closed configuration (FIG. 6) and an open configuration (FIG. 5) by movement of the second array of support members 504e-504h distally. In the open configuration, the first and second array of support members 504a-504h may define an open-ended basket-shaped arrangement, while being biased radially outwards. In contrast, in the closed configuration, the second array of support members 504e-504h may be pulled proximally to close the basket formed by support members 504.

FIG. 6 shows the retrieval device 500 of FIG. 5 in a partially closed configuration. In this embodiment, the second array of support members 504e-504h are pulled proximally, such that loop member 508 forms a folded or compressed shape with a generally zigzag pattern proximal to distal. The retrieval device 500 may be biased towards the open configuration in any manner, such as a radial outward bias or bend in one or more, or all of the support members 504, and/or the loop member 508 being biased to the open loop configuration (FIG. 5).

Figure 8:
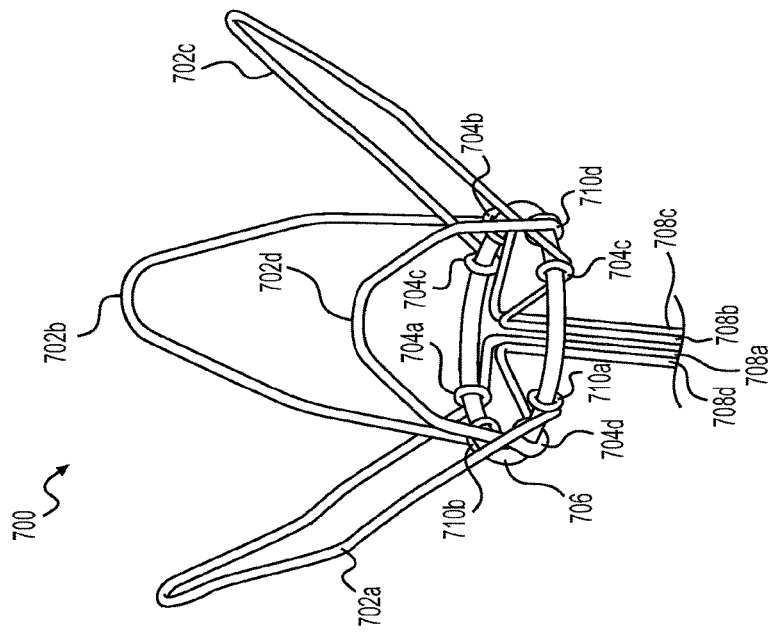
FIG. 8 is a schematic view of the retrieval device of FIG. 7 with the sheath removed and arranged in an open configuration.
Figure 7:
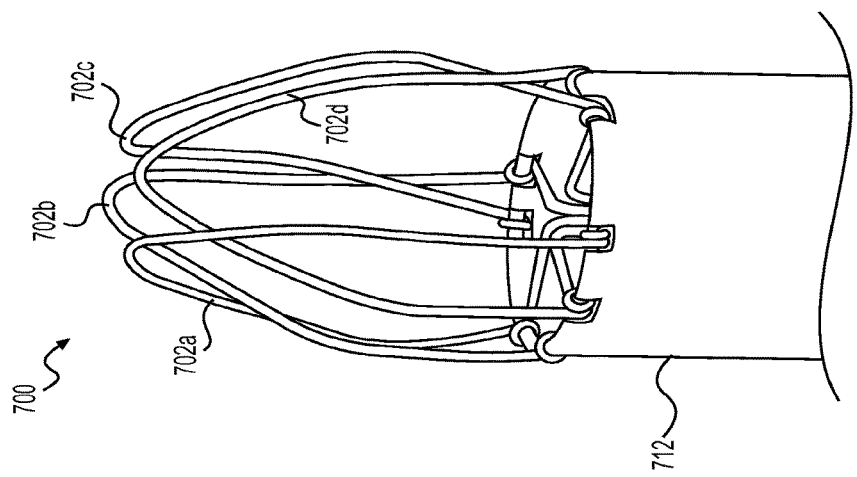
FIG. 7 is a schematic view of a retrieval device according to yet another embodiment of the present disclosure.
Figure 9:
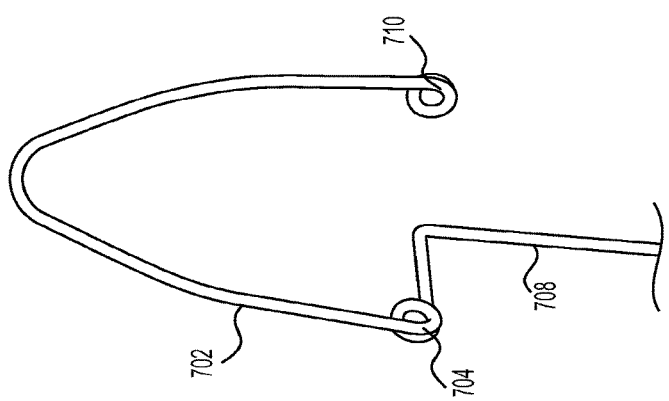
FIG. 9 is a schematic view of an exemplary capture member of the retrieval device of FIG. 7.

FIGS. 7-9 show another exemplary retrieval device 700. The retrieval device 700 may include multiple capture members 702a, 702b, 702c, and 702d (collectively 702), each having a pair of proximal loops or eyelets 704a, 710a, 704b, 710b, 704c, 710c, 704d, and 710d (collectively 704, 710), respectively. The device 700 may further include a loop member 706, extending through the eyelets 704, 710 of the capture members 702. The loop member 706 may have a ring-shaped configuration.

Each capture member 702a-702d may include a longitudinal member 708a-708d (referred to as longitudinal members 708). The capture members 702 may each have longitudinally-extending, petal or cone shaped configurations that pivot about the loop member 706 through proximal loops 704, 710 between a closed configuration (FIG. 7) and the open configuration (FIG. 8). While four capture members 702 are shown in the figures, two, three, five or more capture members 702 may be used. Further, the capture members 702 may be formed of any suitable material including, but not limited to, metals, polymers, or a combination of materials. The stiffness of capture members 702 may be selected so as to support movement from the open to closed configurations. In one embodiment, capture members 702 may include a metal wire. Capture members 702 may have any suitable cross-sectional profile such as, e.g., circular or oval. In some embodiments, portions of capture members 702 may be flattened, machined, extruded, drawn, or etched into a different profile than a remaining portion of capture members 702. In some embodiments, capture members 702 may be pre-bent and/or slotted to allow deflection or directional bending. For example, capture members 702 may be pre-bent radially inward to form the configuration shown in FIGS. 7-9. Alternatively, the capture members 702 may include a distal end bent radially outwardly. The distal most end of the capture members 702 may be rounded as shown or more pointed. In one embodiment, movable member 108 may be formed with a super elastic material or shape memory material, such as, e.g., Nitinol wires having a diameter of about 0.003", although other suitable diameters may alternatively be utilized. The capture members 702 may be bent to flare outward or inward. Capture members 702 may also have different lengths so that not all distal ends align.

The retrieval device 700 may include a sheath 712 (FIG. 7) extending from the capture members 702 to a handle (not shown). The sheath 712 may include a lumen for receiving longitudinal members 708. The sheath 712 may be configured such that the loop member 706 is permanently attached to a distal end of the sheath 712. This attachment can be achieved by a radial lumen formed in the distal end of the sheath 712, as shown in FIG. 7, or in any other conventional way.

As shown in FIGS. 7-9, the proximal loops 704, 710 of the capture members 702 may be attached to the loop member 706 by coiling around the loop member 706. Thus, the capture members 702 are each connected to the loop member 706 at two different, spaced apart, circumferential positions. The capture members 702 may be arranged around the loop member 706 in an alternating fashion such that adjacent capture members have a loop 704 or 710 located between the two loops 704, 710 of a capture member 702. The longitudinal members 708 may first extend generally normal to a longitudinal axis of the device so as to extend radially inwardly from the loop member 706 towards a center of the device 700. Then, the longitudinal members 708 may bend to extend in an axial direction into the sheath (not shown) and terminating at a pull wire or actuation mechanism (such as at a handle). The longitudinal members 708 be coupled to the handle in any conventional manner to allow transmission of a push or pull force to the proximal loops 704.

FIG. 9 shows a single capture member 702 of the retrieval device 700. As shown, the capture member 702 may include two proximal loops 704 and 710, such that the former 704 is coupled to the longitudinal member 708 while being coiled around the loop member 706, whereas the latter 710 merely coils around the loop member 706. The capture members 702 include a distally-extending pedal member having a planar cone shape with a rounded apex. The longitudinal member 708 may extend down to the handle, such that manipulating the handle may pull the capture member 702 to open the retrieval device 700 (as shown in FIG. 8). The capture members 702 may have shaping, sizing, surface modification, notches, bumps, coatings, gripping components and the like to promote capture objects and holding onto objects.

The disclosed retrieval devices, 100, 500, and 700 may provide, among other things, a small profile to assist in delivery and removal, a variable size basket to adjust to variable sized material and deployment locations, and a distal open-ended capture of material to assist in positioning the retrieval device with respect to the material to be captured.

Embodiments of the present disclosure may be applicable to various and different medical or non-medical procedures beyond the procedures disclosed above. In addition, aspects of any one of the aforementioned embodiments may be combined with any other aspect of any other of the embodiments disclosed herein.

Other embodiments of the present disclosure will be apparent to those skilled in the art from consideration of the specification and practice of the embodiments disclosed herein. For example, in any of the above disclosed embodiments, the distally located members (e.g. support members, hollow member, movable members, loop member, and/or capture members) may include features to improve gripping. Such features may include surface modifications such as protrusions, indentations, hooks, bends, and/or coatings. Further, in any of the above disclosed embodiments, the various wires disclosed may include twisted filaments to enhance gripping. Further, the various distal loops (e.g. 106, 506, 704, 710) may be intergrally formed or separate components from is support or capturing member. It is intended that the specification and examples be considered as exemplary only, with a true scope and spirit of the disclosure being indicated by the following claims.

What is claimed is:

1. A retrieval device, comprising:
    a sheath having a distal end and a longitudinal axis;
    a plurality of support members extending distal of the distal end, the support members each having at least one distal loop, wherein at least one of the distal loops of the support members forms at least one biasing coil;
    a hollow member extending distal of the distal end; and
    a movable member extending distally from the hollow member and slidably extending through the distal loops of the support members,
    wherein a first plurality of the support members are longitudinally movable relative to the sheath, and wherein a second plurality of the support members are longitudinally fixed relative to the sheath.

2. The retrieval device of claim 1, wherein at least one of the plurality of support members are biased radially outwardly.

3. The retrieval device of claim 1, wherein the movable member forms a ring shape that lies generally in a plane normal to an axis of the sheath when the device is in an open configuration.

4. The retrieval device of claim 1, wherein the distal loops are located at a distalmost location on the support members.

5. The retrieval device of claim 1, further including at least one biasing member extending between the support members.

6. The retrieval device of claim 5, wherein the at least one biasing member includes a plurality of biasing member coils, each biasing member coil being located along the movable member.

7. The retrieval device of claim 1, further including a mesh extending between at least two support members.

8. The retrieval device of claim 1, wherein the support members and movable member form a distal-open-ended, generally conical shape when the device is in an open configuration.

9. The retrieval device of claim 1, wherein the movable member is slidably disposed within the hollow member to move between an open configuration and a closed configuration.

10. A retrieval device, comprising:
    a sheath having a distal end and a longitudinal axis;
    a plurality of support members extending distal of the distal end, each of the support members having a distal loop; and
    a loop member extending through the distal loops of the support members,
    wherein a first plurality of the support members are longitudinally movable relative to the sheath, and wherein a second plurality of the support members are longitudinally fixed relative to the sheath.

11. The retrieval device of claim 10, wherein at least one of the longitudinally movable support members is longitudinally movable through action on an actuator.

12. The retrieval device of claim 10, wherein the loop member forms a ring shape that is permanently attached to each of the distal loops.

13. The retrieval device of claim 10, wherein the support members are biased outwardly.

14. The retrieval device of claim 10, wherein the support members and loop member form a distal-open-ended, generally conical shape when the device is in an open condition, and the loop member has a generally zigzag shape in a closed condition.

15. The retrieval device of claim 10, wherein at least one of the longitudinally fixed support members is longitudinally fixed to the distal end of the sheath.

16. The retrieval device of claim 15, wherein the plurality of support members are circumferentially arranged and alternating support members are longitudinally fixed and alternating support members are longitudinally movable.

17. A retrieval device, comprising:
    a sheath having a distal end;
    a plurality of capture members extending distal of the distal end, each of the capture members having at least two proximal loops and each of the capture members having a longitudinal member coupled to at least one of the proximal loops; and
    a loop member extending through the proximal loops of the capture members,
    wherein the capture members are arranged such that one of the proximal loops of a first capture member is positioned between the at least two proximal loops of an adjacent capture member.

18. The retrieval device of claim 17, wherein the loop member includes a ring member, and the capture members are coupled to the ring at a plurality of spaced circumferential positions corresponding to the location of the proximal loops.

19. The retrieval device of claim 17, wherein the capture members pivot about the ring to move between an open condition and a closed condition.

* * * * *